US006277019B1

(12) United States Patent
Veldkamp et al.

(10) Patent No.: US 6,277,019 B1
(45) Date of Patent: Aug. 21, 2001

(54) METHOD AND APPARATUS FOR REMOVING FAT FROM MEAT CUTS

(75) Inventors: Brent M. Veldkamp, Cumming; R. Thomas Seaberg, Des Moines; Don D. Holms, West Des Moines; Doug McCloskey, Altoona, all of IA (US)

(73) Assignee: Townsend Engineering Company, Des Moines, IA (US)

( * ) Notice: Subject to any disclaimer, the term of this patent is extended or adjusted under 35 U.S.C. 154(b) by 0 days.

(21) Appl. No.: 09/552,396

(22) Filed: Apr. 19, 2000

(51) Int. Cl.[7] .................................................... A22C 17/12
(52) U.S. Cl. ............................................ 452/134; 452/127
(58) Field of Search ..................................... 452/134, 127

(56) References Cited

U.S. PATENT DOCUMENTS

| | | | |
|---|---|---|---|
| 3,613,154 | 10/1971 | Townsend . | |
| 3,789,456 | 2/1974 | Doerfer et al. . | |
| 4,246,837 * | 1/1981 | Chenery | 452/134 |
| 4,628,806 | 12/1986 | Murphy | 99/486 |
| 4,970,755 * | 11/1990 | Leblanc | 452/134 |
| 4,979,269 * | 12/1990 | Norrie | 452/134 |
| 5,090,939 | 2/1992 | Leblanc | 452/127 |
| 5,429,548 | 7/1995 | Long et al. | 452/127 |
| 5,476,417 | 12/1995 | Long et al. | 452/127 |
| 5,738,577 | 4/1998 | Long | 452/127 |
| 6,129,625 * | 10/2000 | Cate et al. | 452/134 |

FOREIGN PATENT DOCUMENTS

| | | |
|---|---|---|
| 0 422 877 B1 | 12/1990 | (EP) . |
| 0 484 933 B1 | 3/1994 | (EP) . |

* cited by examiner

*Primary Examiner*—Willis Little
(74) *Attorney, Agent, or Firm*—Zarley, McKee, Thomte, Voorhees & Sease

(57) ABSTRACT

A method for removing a portion of fat from meat cuts involves placing a meat cut on a longitudinal conveyor, pressing sensor probes into the meat cut to measure the relative thickness of fact and the location of lean in the meat, and then withdrawing the sensor probes from the meat. An electronic signal is transmitted from the sensor to a controller along with an encoder signal to determine the depth from the outer lower surface of the meat cut through a layer of fat in the meat to a layer of lean in the meat. Data taken from the foregoing step determine the desired position of the blade. A predetermined amount of fat is thereupon cut from the meat cut by the blade. An apparatus for removing a portion of fact from meat cuts includes a frame and at least one sensor probe including fiber optics to permit scanning of the interior of a meat cut penetrated by the probe. Power for moving the probe into the meat is mounted on the frame along with a skinning blade mounted in a path of movement of a meat cut on the frame. A controller on the frame takes data from the sensor probe and determines the linear depth of fat material on the meat cut and lean material in the meat cut. The controller then determines the operating position of the blade and positions the blade to effect the removal of the desired amount of fat.

14 Claims, 8 Drawing Sheets

24A
4A-4A
20
70
68
64
12
18
78
46
12
40
10
16
12
24
14

14
16
18
20
22
24
28
32
34
36
46
50
52
56
60
62
74
94
96
100
102
104
114
121
121A
A
B
C

METHOD AND APPARATUS FOR REMOVING FAT FROM MEAT CUTS

BACKGROUND OF THE INVENTION

In the production of processing meat cuts, such as pork butts, existing specifications require that sufficient fat be removed from the butt to expose six to eight square inches of lean meat, while leaving ⅛th to ¼th of an inch fat cover on the remaining curved surface of the meat cut.

Existing machines and methods for achieving the above specification involve safety hazards and inaccurate cutting which results in waste of meat product. Further, more than one trimming operation is normally required to achieve the needed specification. Existing processes are labor intensive.

Until now, the process of removing an optimal amount of fat from meat cuts such as pork butts has required a person who makes repeated cuts until the desired amount of lean meat is exposed. Often this results in waste, as it is impossible to tell without cutting into it at what depth the lean starts and the fat stops.

Previous attempts at automating this process have met with failure because of the variation in fat cover on the meat cuts. The fat cover on meat cuts typically has a layer of lean running through it, which starts about halfway between the neck and the back which is called the false lean. The fat cover is normally thinnest at the neck edge and fattest at the back edge. It is customary when preparing such meat for sale to remove a wedge-shaped piece of fat in order to expose the "false lean". Typically in the industry, enough fat should be removed to expose at least six square inches of lean meat.

It is therefore a principal object of this invention to provide an apparatus for removing a portion of fat from meat cuts which is safe, accurate, and efficient both from a standpoint of time and labor involved.

It is a further object of the invention to provide for the photometric determination of the layers of fat and lean within individual pieces of meat for the purpose of guiding the automated removal of optimal amounts of unwanted material by means of an optical device located within a specially constructed probe.

These and other objects will be apparent to those skilled in the art.

SUMMARY OF THE INVENTION

A method for removing a portion of fat from meat cuts involves placing the meat on a longitudinal conveyor, pressing sensor probes into the meat to measure the thickness of fat and the location of lean therein, and then withdrawing the sensor probes therefrom. An electronic signal is transmitted from the sensor probes to a controller and encoder to determine the depth from the outer lower surface of the meat through a layer of fat therein to a layer of lean. Data taken from the foregoing step determine the desired position of the cutting blade. A predetermined amount of fat is thereupon cut from the meat by the blade. The method is used to determine in meat the layer thicknesses by recording at uniform intervals during the penetration into the meat the reflectance values. The reflectance values are mapped against the distance traveled by the probe will show segment thickness.

An apparatus for removing a portion of fat from meat cuts includes a frame and at least one sensor probe including fiber optics to permit scanning of the interior of a meat cut penetrated by the probe. Power for moving the probe into the meat is mounted on the frame along with a skinning blade mounted in a path of movement of a meat cut on the frame.

A controller on the frame takes data from the sensor probe and determines the linear depth of fat material on the meat cut and lean material in the meat cut. The controller then determines the operating position of the blade and positions the blade to effect the removal of the desired amount of fat.

More specifically, a meat piece is conveyed on a conveyor belt towards the cutting device. The frame supports the probes beneath the conveyor of the meat. As soon as the meat rides over the probe path, the meat pauses, an air cylinder activates and the probes penetrate the meat. The optic fibers for reception and transmission of the signals are threaded through the probes. The probes have a probe window at the distal end. An LED sends light through a first set of fibers in the probes. The receiving signals picked up by the receiving optical fibers send a message to the controller which analyzes the signals. The probes take measurements while they are engaged with the meat piece both on the up and the down stroke. They are immediately withdrawn and the meat piece travels further into engagement with the skinning mechanism. The signal analysis generates a message, which is used by the blade control device to raise or lower the blade from the pulling surface of the skinning mechanism, resulting in the removal of a piece composed primarily of fat.

The difference in reflective potential between the fat and lean muscle is distinct enough that a simple probe containing optical fibers can easily distinguish between them. This information is relayed to a controller which controls the contours of a blade which is in a skinning machine well-known in the industry.

The controller makes a determination based on the registration of a large number of values of reflection from a single wavelength at intervals of depth in the piece of meat. In addition, all values are used and inserted in to a suitable equation or equation system, which is a multi-variable algorithm for the calculation of layer thicknesses.

The multivariable algorithm includes a preset offset distance which accounts for the distance between the cutting blade and toothroll in the minimum cutting position, and a variable offset which can be modified by the operator to customize the product appearance according to this customer specifications.

In addition, the algorithm includes other variables to vary the desired cutting depth at different times during the cut. For example, the cutting depth may be decreased during the first one-third of the meat to increase the resulting fat depth on the finished product. During the second one-third of the meat the cutting depth may be at the calculated depth. During the last one-third of the meat, the cutting depth may be increased to remove more fat in that area.

The meat may be placed at different lateral locations on this conveyor belt to allow a portion of the meat to be cut by the curved section of the blade rather than this flat section. This varies the depth of fat removed from the outside edges of the meat, and allows meat cuts from both the left and right sides of the hog, for example, to be defatted in one machine.

The cutting device includes a toothroll, shoe and curved blade holder. The blade holder is fastened to a short section of shoe. The blade holder provides the desired curved cut, while the shoe/toothroll provides the means to pull the meat through the blade. The blade height adjusting mechanism is actuated electromechanically. The gripper roll and exit conveyor drive rotate continuously. The conveyor system must move the meat through the stations, and present it to the cutting device. It indexes, so the meat is stationary when being probed. The conveyor belt is modular to ensure positive indexing. The stations are marked by blue segments on the belt. The stations are a set distance apart. During indexing, the belt accelerates for a set distance, moves at a constant speed a set distance (the approximate length of the meat cut), then decelerates a set distance. The maximum, constant speed of the conveyor matches the speed of the toothroll while the meat is moving through the cutting device. The conveyors must hold the meat securely during probing, and maintain its position through the cutting device so that the depth cut is consistent with the depth measured by the probe. A pivoting, flat top plate positioned just ahead of the blade alternately presses the front end and the back end of the meat into the shoe/toothroll/blade to ensure that the meat gets a good start and finish. An alternate pivoting, curved top plate is used to press the outside edges of the meat into the toothroll for better cutting performance.

DESCRIPTION OF THE PREFERRED EMBODIMENT

Figure 1:
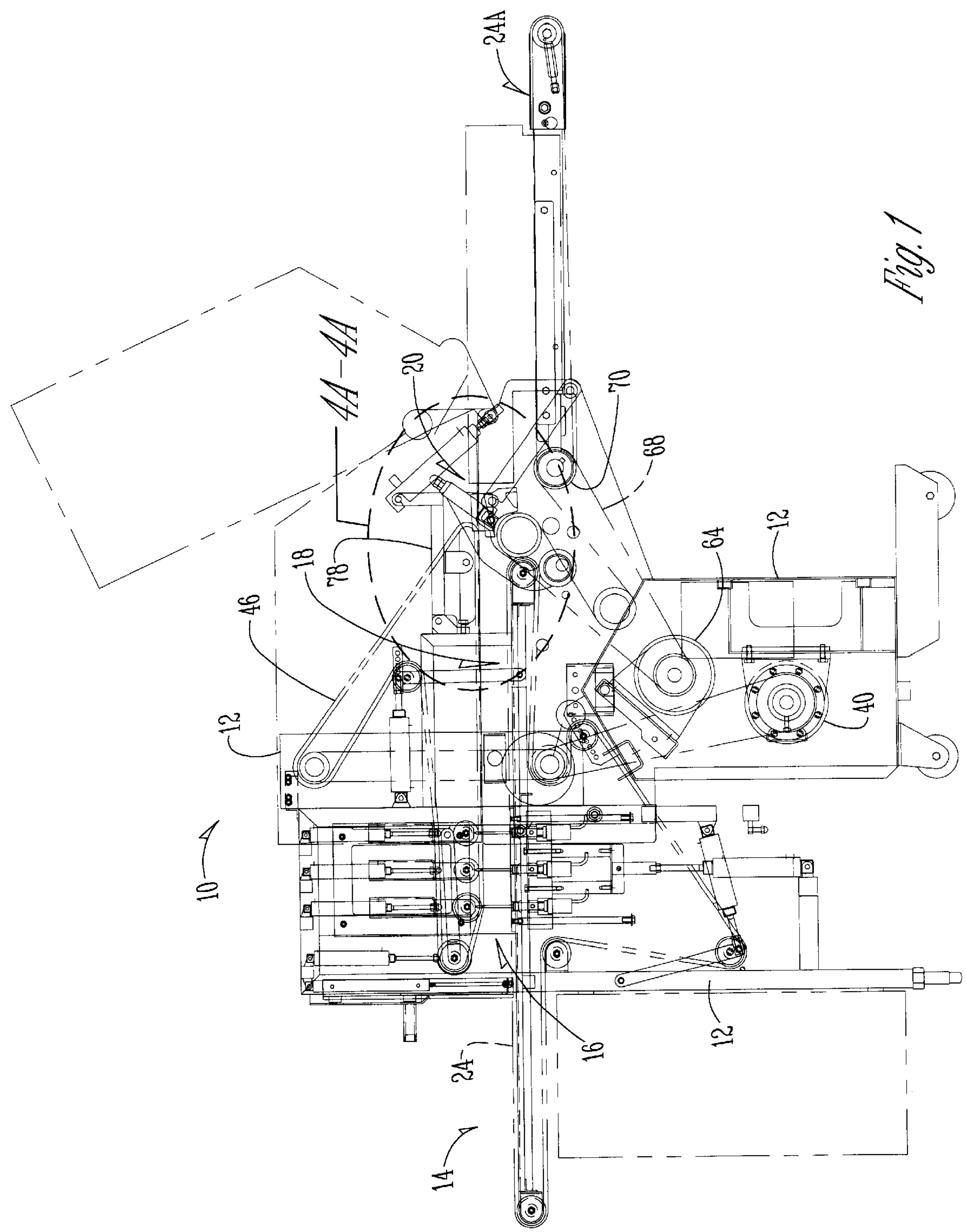
FIG. 1 is a side elevational view and partial sectional view of the apparatus of this invention.

The machine 10 has a frame 12, (FIG. 1), with a loading station 14, a probing station 16, a waiting station 18, and a skinning station 20 (FIGS. 3A–3D).

Figure 2:
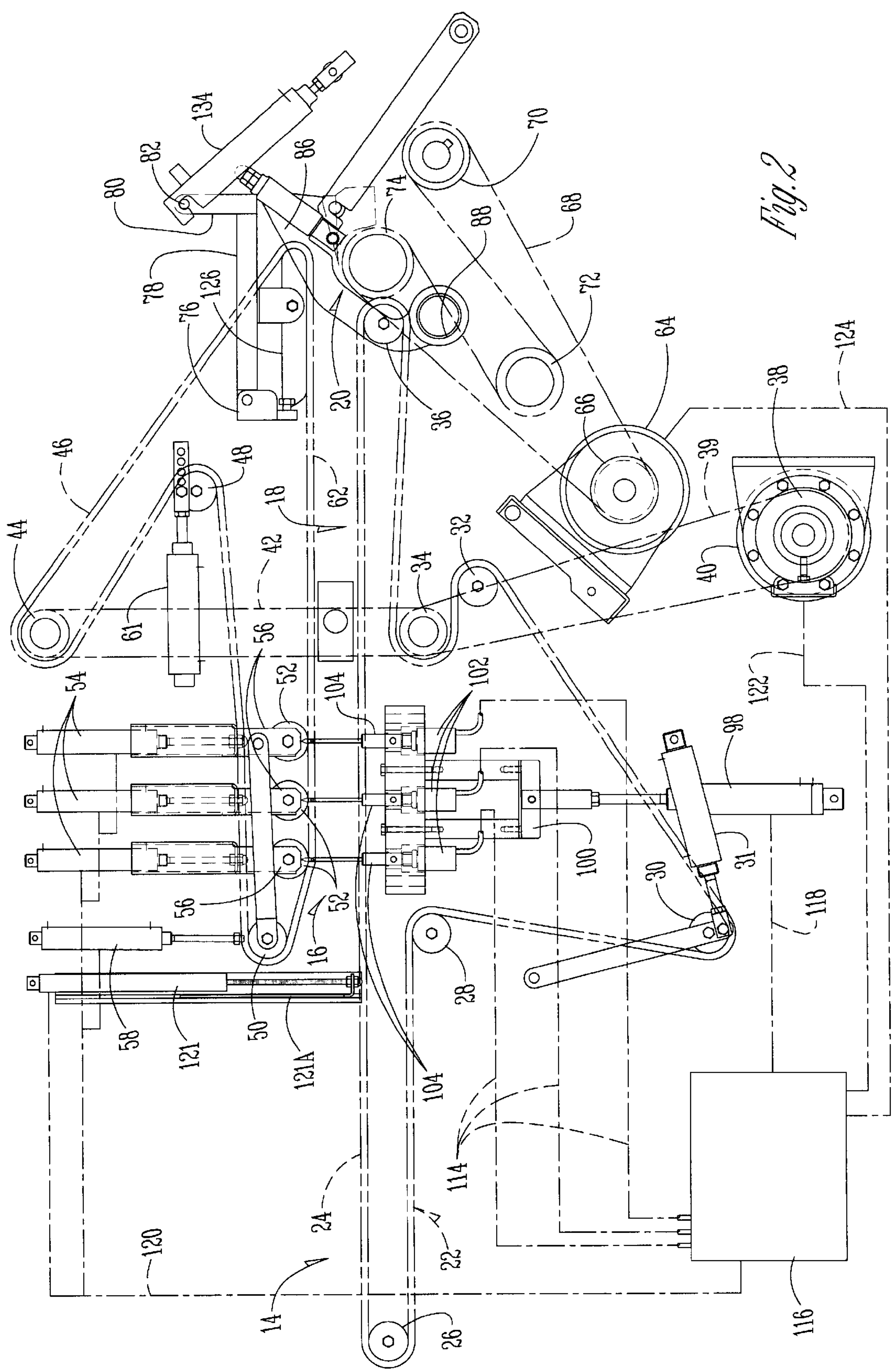
FIG. 2 is an enlarged scale layout of the power train of the apparatus of FIG. 1.

With reference to FIG. 2, a conveyor belt 22 is mounted on frame 12 and has a top horizontal portion 24. A horizontal transverse roll 26 is mounted adjacent the loading station 14 to support and reverse the direction of conveyor belt 22. The belt 22 then extends to roll 28 and extends therearound and departs in a downwardly direction towards roll 30. A conventional piston-belt-type tightener 31 is associated with roll 30 to selectively tighten or change the attitude of belt 22.

The belt 22 then departs roll 30 and extends upwardly and forwardly to roll 32 which is slightly below and forwardly of roll 34. The belt extends around roll 32 and thence rearwardly and then again forwardly as it extends around roll 34. The belt then extends to forward roll 36 and departs roll 36 back in a horizontal direction towards the point beginning at roll 26. A motor 38 (FIG. 2) is mounted on frame 12 and is connected by belt 39 to the roll and drive pulley 34 via pulley 40 on the motor.

With reference to the upper portion of FIG. 2, a chain 42 extends from roll and drive pulley 34 upwardly around a roll and drive pulley 44. A conveyor belt 46 extends around roll 44 and departs therefrom in a forwardly and downwardly direction to extend around roll 48. The belt 46 then extends rearwardly to extend around roll 50, and departs roll 50 in a forwardly horizontal direction. Belt 46 engages a plurality of rolls 52 which are mounted on the lower end of piston assemblies 54 which are mounted on downwardly extending brackets 56. Air piston 58 is parallel to the vertical air pistons 54 and is operatively connected to roll 50. Pistons 54 and 58 serve to raise and lower the belt 46 with respect to the horizontal portion 24 of belt 22 which extends thereunder. Belt 46 then extends forwardly from rolls 52 to extend around plate 126, whereupon the belt then extends rearwardly and upwardly to its point of beginning at roll 44. A conventional piston-belt tightener 61 (FIG. 2) is associated with roll 48 to facilitate the adjustment of the tension on conveyor belt 46. Roll 48 serves also as a pivot point for the upward and downward movement of the belt 46 by the pistons 54 and 58. The lower horizontal train of belt 46 as seen in FIG. 2 is identified by the numeral 62.

A motor 64 is mounted on frame 12, (FIG. 2), and has an output drive pulley 66. A belt 68 extends from pulley 66 and extends forwardly and upwardly to extend around pulley 70. The belt 68 then extends rearwardly and downwardly around pulley 72, and thence upwardly and forwardly around a drive pulley (not shown) on gripper roll 74 which is a part of the skinning station 20 as will be discussed hereafter.

Figure 4:
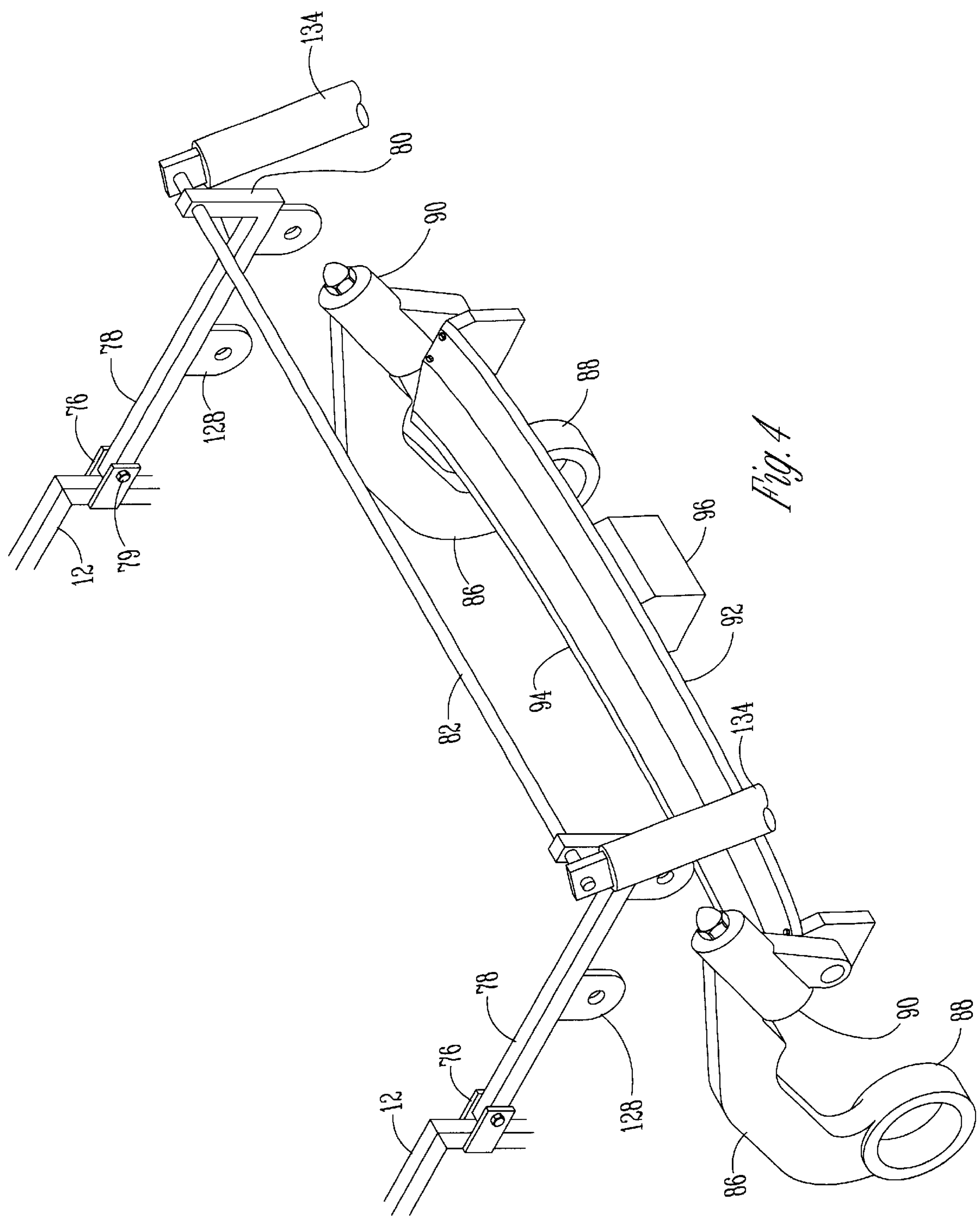
FIG. 4 is an enlarged scale perspective view of the cutting station of the device in FIG. 1.

Brackets 76 (FIG. 4) are spaced apart and are secured to frame 12 and are pivotally secured to arm 78 by the rearward ends of the arms through the function of conventional connecting pins 79. A vertical arm segment 80 extends upwardly from the forward end of the arm 78 (FIGS. 2 and 4). A transverse rod 82 extends between the upper ends of arm segments 80. Separate springs 134 are secured to the rod 82 and extend forwardly to frame 12 to yieldingly prevent the upward pivotal movement of arms 78 on pins 79.

Figure 3A:
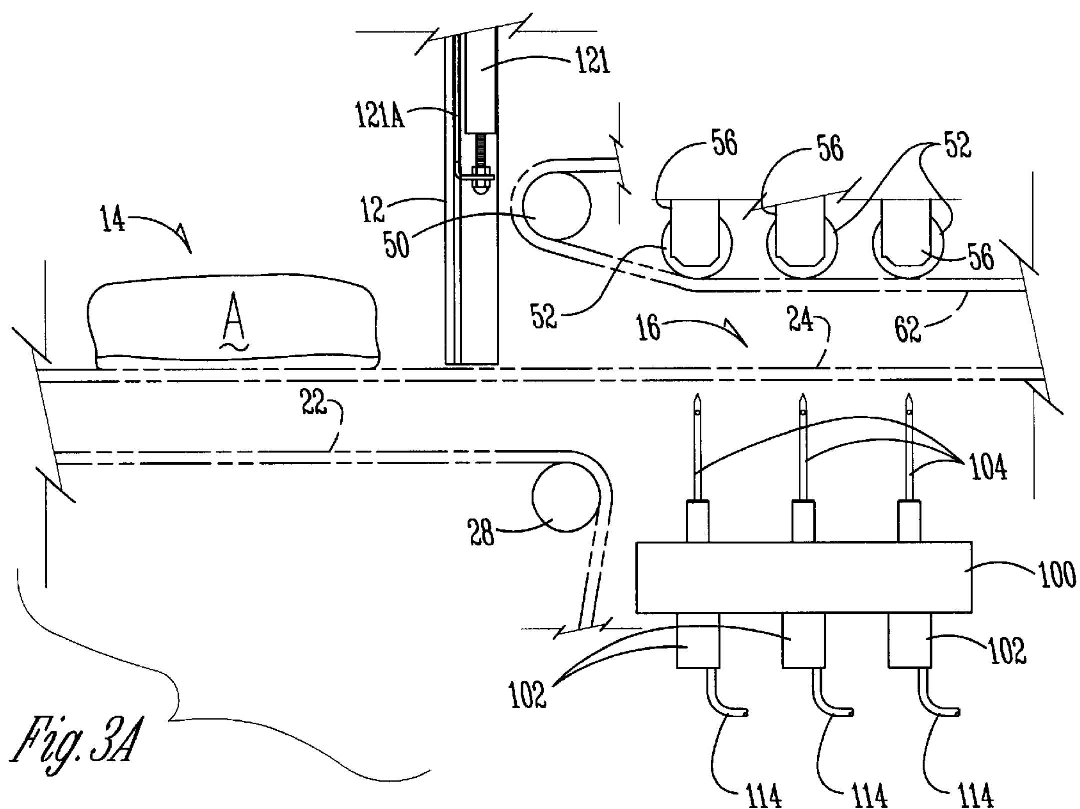
FIGS. 3A–3D are schematic elevational views showing the sequential steps of the method of this invention as practiced on the apparatus of this invention.

A pair of blade arms 86 (FIG. 4) are attached at their lower ends to sleeve 88 (FIG. 2) which are mounted on rotatable cams (not shown) which can raise or lower the blade arms. Blade mounts 90 are an integral part of arms 86 and conventionally are connected to the ends of curved blade holder 92 (FIG. 4). A blade 94 (FIGS. 3C and 3D) is secured to the blade holder 92 and is conventionally associated with arcuate-shaped shoe 96 to perform the skinning operation (FIGS. 3C and 3D).

Figure 5:
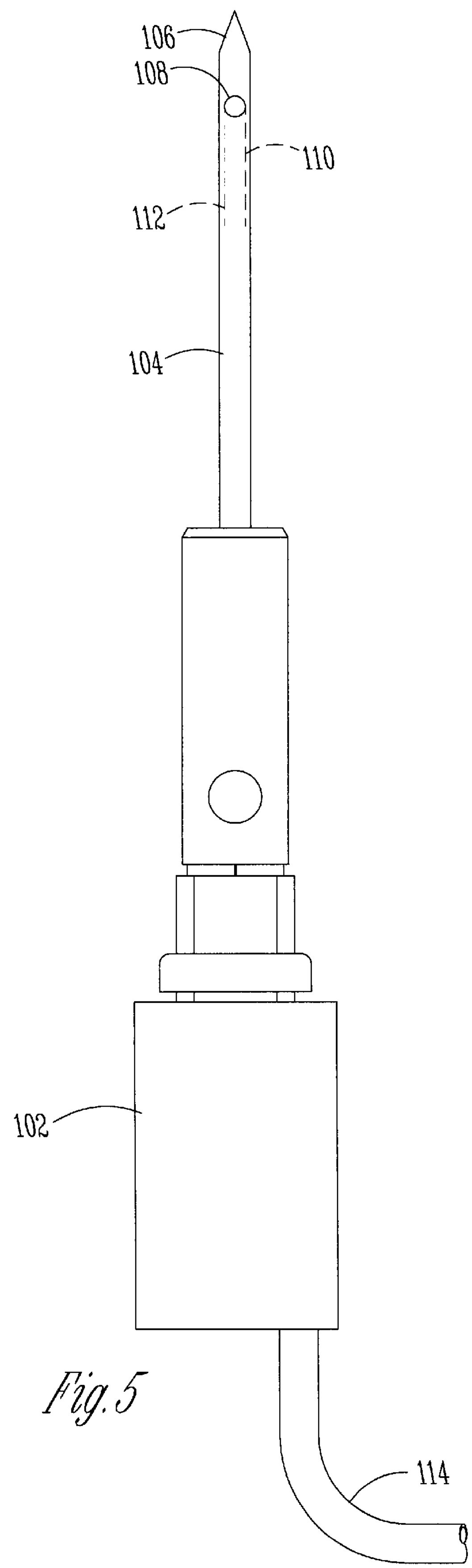
FIG. 5 is an elevational view at an enlarged scale showing one of the probe sensors.
Figure 6:
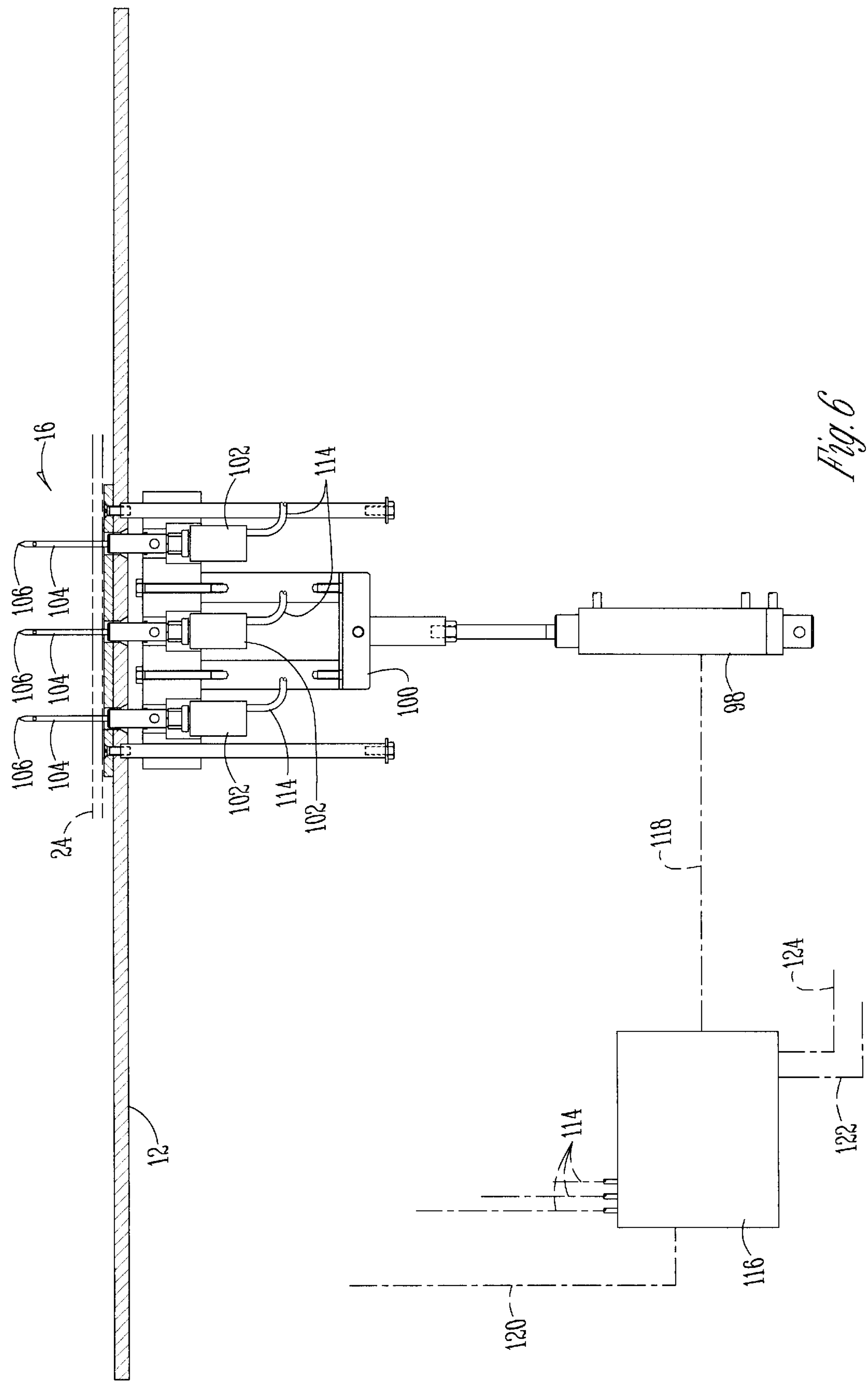
FIG. 6 is an enlarged scale side elevational view of the apparatus at the sensor station of this invention.

As shown in FIG. 2, a piston assembly 98 is shown in the lower portion of that FIG. and is vertically disposed and is operatively connected to bracket 100. Three probe sensors 102 are vertically disposed on bracket 100 and extend upwardly therefrom and terminate in elongated probe spikes 104 (FIGS. 5 and 6). The spikes terminate at their upper ends in points 106. Each spike has a window opening 108. As shown in FIG. 5, two sets of optical fibers 110 and 112 extend through probes 102 and spikes 104 and terminate immediately adjacent the window opening 108. Optical fibers 110 are connected to a source of light in the sensor 102 to illuminate the area just outside the spike and outside the window opening 108. Optical fibers 112 have the ability to receive light that is reflected from the lean and fat portions of the meat cut being treated. The light coming from fibers 110 and reflected onto the fibers 112 from the lean and fat surfaces are returned to sensor 102 which sends a signal through lead 114 (FIG. 5) to a controller 116 (FIG. 2) including a computer. With reference to FIGS. 2 and 6, a lead 118 connects controller 116 with the piston assembly 98. Lead 120 extends from controller 116 to a slidable door 121/A and linear actuator 121 (FIGS. 2 and 3C) located just forwardly of loading station 14. Lead 120 also connects controller 116 to pistons 54 and 58. Lead 122 connects controller 116 with motor 38 (FIG. 2). Lead 124 connects controller 116 with motor 64.

Figure 4A:
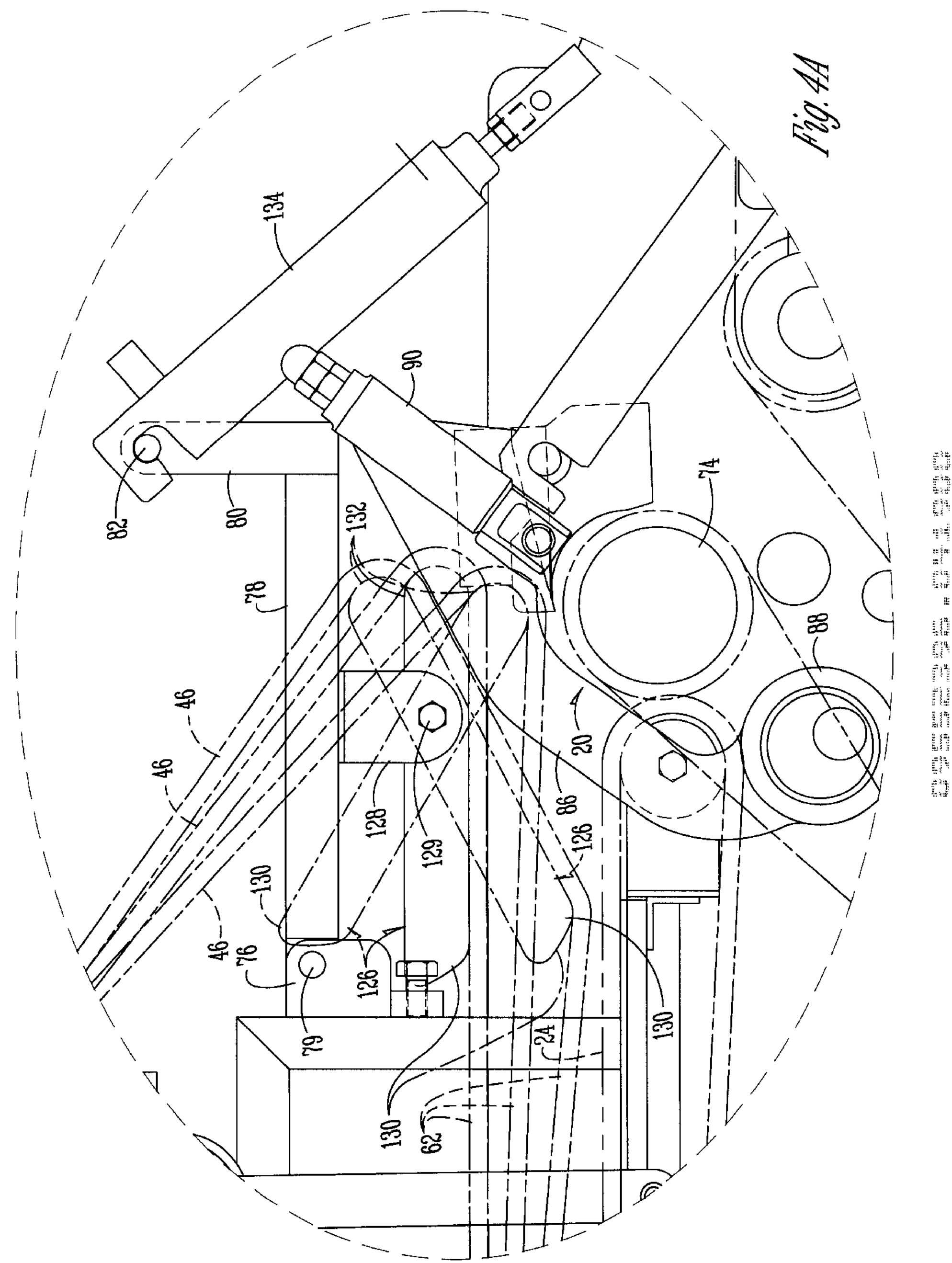
FIG. 4A is an enlarged scale side elevational view of the cutting station as shown in FIGS. 1 and 2.

With reference to FIG. 4A, a top feed plate 126 of rectangular and generally flat construction is rotatably supported by ears 128 on arm 78 (FIG. 4). An encoder (not shown) measures the position of the probes and transmits this measurement to the controller. Pins 129 effect the pivotal connection between plate 126 and the ears 128. Feedplate 126 has a leading end 130 and a trailing end 132. A spring cylinder 134 has an upper end that hooks on rod 82 and a lower end secured to the frame 12 and serves to hold feedplate 126 down on the meat cut.

The feedplate 126 is normally in the horizontal position shown by the solid lines in FIG. 4A. The lead end 130 pivots upwardly as the meat product endeavors to pass thereunder on conveyor 24. This causes the trailing end 132 to move to a level lower than the pin 129 whereupon it exerts force on the meat product as that product moves into contact with the gripping roll 74 and the blade 94. The continued longitudinal movement of the meat towards the blade then causes the meat product to push upwardly on the depressed trailing end 32 which causes the plate 126 to move to the position shown in FIG. 4A where the end 130 is depressed or lowered. The engagement of the product by the lower end portion 130 of the plate member serves to exert additional longitudinal boost to the meat product as it is moving upwardly and over the blade 94 and gripping roll 74 at the skinning station 20.

In operation, a meat cut A (FIG. 3A) is placed on the conveyor belt 22 at the loading station 14. The controller 116 has the ability to index the movement of conveyor 22, and the conveyor is motionless at this point in time. The door 121 is in an open position. The bracket 100 is in its lower position shown in FIG. 3D so that the probe spikes 104 are withdrawn and the points 106 of the spikes 104 are at a level below the lower horizontal portion 24 of belt 22.

Figure 3B:
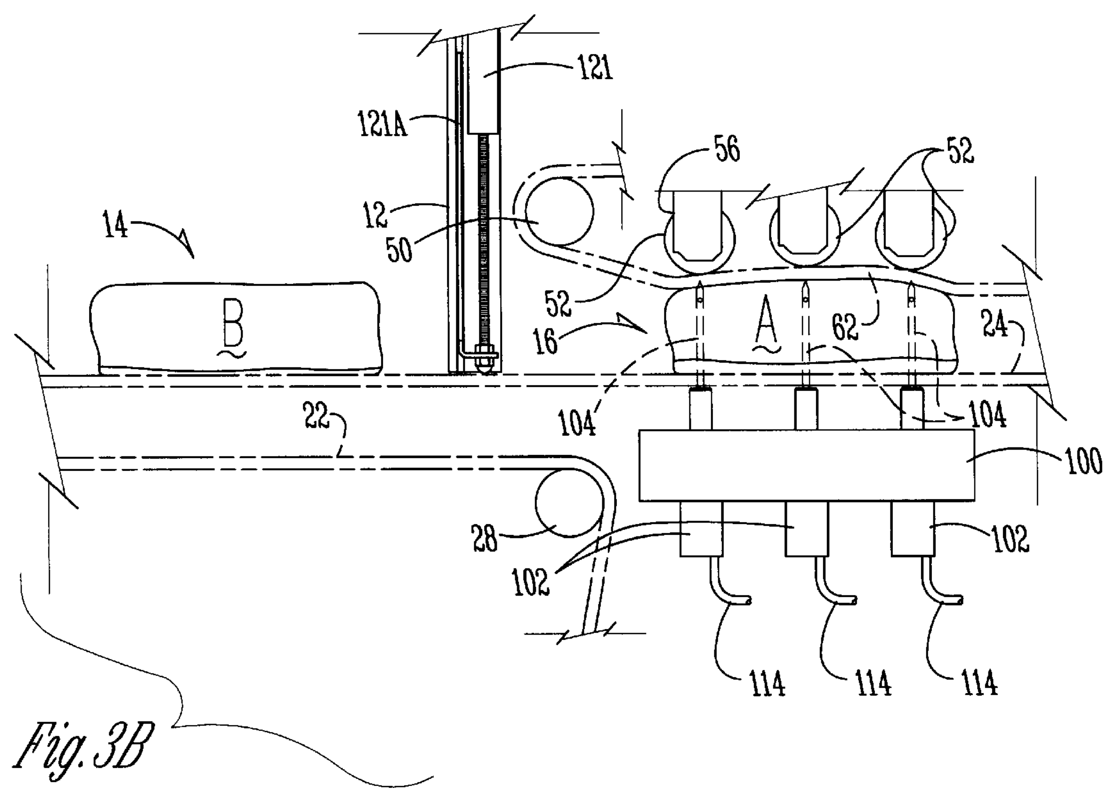
Figures 3C, 3D:
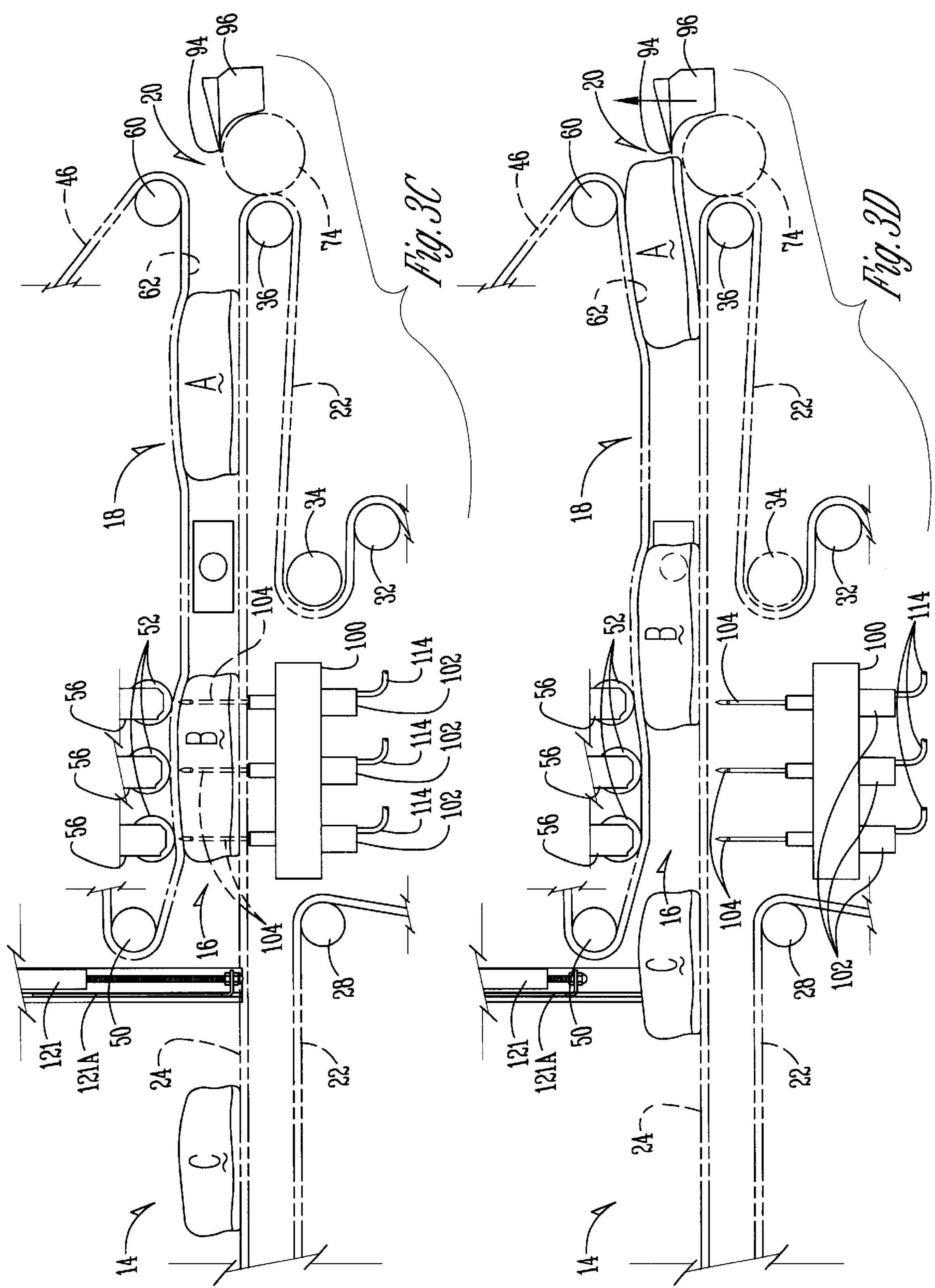

The controller 116 thereupon actuates motor 38 to cause conveyor belt 22 to advance in a clockwise direction as seen in FIG. 2 whereupon the meat cut A is moved to the probing station 16 (FIG. 3B). The controller then closes door 121A, and actuates the piston assembly 98 which causes the bracket and sensors 102 to rise whereupon the probe spikes 104 penetrate the meat cut A as shown in FIG. 3B. The pistons 54 and 58 are also actuated by the controller 116 to press down on the meat cut A as shown in FIG. 3B while the probe spikes 104 are penetrating the meat A. At the same time, meat cut B can be placed on the loading station 14.

The probe spikes move quickly upwardly and thence downwardly out of the meat product. The sensor 102 works in the manner described and permits the optical fibers 112 to receive the reflected light from optical fibers 110 through the window opening 108, with the reflected light being of varying intensity depending on whether the light is reflected from fat or lean meat. A signal from the reflected light through fiber optics 112 is transmitted through line 114 to controller 116 and the encoder (not shown) so that the relative thickness of the fat and lean meat is determined by the controller. Obviously, the conveyor 22 is motionless during the time when the penetration of meat cut A is penetrated by the probe spikes 104 at the probing station depicted in FIG. 3B.

The probe spikes 104 move quickly into and out of the meat cut and assume the position generally shown in FIG. 3A at a point below the conveyor belt 22. The controller 116 then opens the door 121, and advances the conveyor belt 22 to the position shown in FIG. 3C where the meat cut A is moved to the waiting station 18, and the meat cut B is moved from the waiting station 14 to the probing station 16. A new meat cut C can be placed at the loading station 14 during this same period of time. FIG. 3D shows how the controller 116 further indexes the conveyor belt 22 after the above described description of the components in FIG. 3C. This causes the meat cut A to move to the cutting station 20; the door 121 opens to receive the meat cut C; and the meat cut B moves towards the waiting station 18. It should be noted that the controller also causes the lower horizontal portion 62 of belt 46 to engage the top of meat product A as it moves into the cutting station (FIG. 3D). At the same time, the feedplate 126 engages the meat cut A and performs its boosting function of pushing the meat A through the skinning station as described heretofore.

Critical to the foregoing process is that the controller 116 receives a signal generated from fiber optics 112 to cause the blade 94 to cut the meat cut A passing through the skinning station 20 at a sufficient depth that the fat will be removed at a depth to expose at least six square inches of lean meat. The blade 94 will be at the appropriate depth by virtue of the measurements of sensor 102 transmitted to controller 116 and the encoder (not shown) to cause the blade 94 to be at a depth calculated by the controller. The controller carries out a calculation and transmits a signal to cause a cam shaft (not shown) to rotate within sleeves 88 causing blade arms 86 to adjust the height of blade holder 92 and blade 94 to a depth with respect to gripper roll 74 to cause the blade to be positioned at the correct height.

It is therefore seen that this invention will achieve at least all of its stated objectives.

What is claimed is:

1. A method for removing a portion of fat from meat cuts, comprising, placing a meat cut on a longitudinal conveyor, pressing sensor probes into the meat cut to measure the thickness of fat and the location of lean in the meat cut, and then withdrawing the sensor probes from the meat, taking an electronic signal from the sensor probes and determining the depth from an outer lower surface of the meat cut through a layer of fat in the meat cut to a layer of lean in the meat cut, taking data from the preceding step and adjusting the height of a blade to a predetermined height with respect to the meat cut to remove a portion of fat from the meat cut to expose a given area of lean, and cutting the portion of fat from the meat cut, the data is acquired by first optic fibers carrying light internally to the probes being pressed into the meat cut to emit light on an internal part of the meat cut into which the probe is being pressed, and second fiber optics in the probe to receive light from the first fiber optics that are reflected from the meat cut.

2. The method of claim 1 wherein the meat cut is placed on a loading station of a longitudinal conveyor, longitudinally moving the meat cut with the conveyor to a probing station; stopping the longitudinal movement of the meat cut, and pressing the sensor probes into the meat cut at the probing station.

3. The method of claim 2 wherein the meat cut is pressed against the conveyor at the probing station and the probes are pressed into the meat cut from below.

4. The method of claim 1 wherein the meat cut is detained at a waiting station while the blade is being adjusted.

5. The method of claim 1 wherein the meat cut is compressed while the portion of fat is being cut from the meat cut.

6. An apparatus for removing a portion of fat from meat cuts, comprising, a frame, at least one sensor probe having an elongated probe spike and including fiber optics to permit scanning of the interior of a meat cut penetrated by the probe spike, a probing station on the frame, means for moving the probe spike of the sensor probe into and out of a meat cut at the probing station, an elongated skinning blade mounted on the frame, a control on the frame operationally connected to the sensor probe for receiving data from the sensor probe to determine the linear depth of fat exterior material on the meat cut, and means on the control for evaluating the data to determine the operating position of the blade to effect the removal from the meat cut of a predetermined amount of fat, and for moving the blade to that operating position.

7. The apparatus of claim 6 wherein a continuous conveyor is on the frame for intermittently moving a meat cut from the probing station to a position for being cut by the blade.

8. The apparatus of claim 6 wherein the control is operatively connected to the conveyor for moving the meat cut.

9. The apparatus of claim 8 wherein a meat cut on the conveyor can first be moved from a loading station to the probing station, and thence to a waiting station; and thence to a cutting station, with the blade being positioned at the cutting station.

10. The apparatus of claim 6 wherein hold down elements are adjustably mounted on the frame above the probe station and a cutting station, with the blade being positioned at the cutting station, the control being operationally secured to the hold down elements to cause them to be intermittently engageable with a meat cut at the probe and cutting stations.

11. The apparatus of claim 9 wherein the control indexes the movement of the conveyor intermittently to move a meat cut on the conveyor from one station to the next succeeding station.

12. The apparatus of claim 9 where a pivotal plate is mounted on the frame adjacent the cutting station to engage a meat cut passing therethrough to provide an additional impetus to the meat cut to move into engagement with the blade and through the cutting station.

13. A probe for measuring the depth of fat and lean portions in a meat cut, comprising, an elongated housing having first and second ends, a hollow probe spike extending longitudinally outwardly from the first end of the housing and terminating in a sharpened outer end, a window opening in the spike adjacent its sharpened outer end, a first set of optic fibers in the housing extending into the spike and having outer ends terminating adjacent the window opening, the first set of optic fibers having inner ends in communication with a light source to transmit light through the first set of optic fiber to illuminate through the window the fat and lean portions of a meat cut into which the spike penetrates, a second set of optic fibers in the housing having inner ends connected to a sensor, and outer ends terminating adjacent the window in the spike to receive light reflected from the fat and lean portions transmitted to the portions from the outer ends of the first set of optic fibers, to permit the sensor to signal the computer when the probe encounters lean meat within the meat cut.

14. The apparatus of claim 6 wherein the skinning blade is mounted in a curved blade holder attached to a shoe assembly at a skinning station, a blade height adjusting mechanism on the frame operatively connected to a control mechanism, and a gripper roll and shoe assembly on the frame adjacent the skinning blade, the speed of movement of the conveyor and gripper roll being substantially equal, and the conveyor engageable with a meat cut at the skinning station to hold the meat cut in a constant orientation while being moved through the skinning station so that the depth of cut is consistent with the depth measured by the probe.

* * * * *